(12) United States Patent
Nieuwenhuis et al.

(10) Patent No.: US 11,519,923 B2
(45) Date of Patent: Dec. 6, 2022

(54) ANALYTE DETECTION SYSTEM AND METHOD

(71) Applicant: SIEMENS HEALTHINEERS NEDERLAND B.V., The Hague (NL)

(72) Inventors: Jeroen Hans Nieuwenhuis, Waalre (NL); Markus Hendrikus Van Roosmalen, Berkel-Enschot (NL); Per Venge, Uppsala (SE)

(73) Assignee: Siemens Healthineers Nederland B.V., The Hague (NL)

( * ) Notice: Subject to any disclaimer, the term of this patent is extended or adjusted under 35 U.S.C. 154(b) by 1020 days.

(21) Appl. No.: 16/307,677

(22) PCT Filed: Jun. 19, 2017

(86) PCT No.: PCT/EP2017/064913
§ 371 (c)(1),
(2) Date: Dec. 6, 2018

(87) PCT Pub. No.: WO2017/220483
PCT Pub. Date: Dec. 28, 2017

(65) Prior Publication Data
US 2020/0182894 A1    Jun. 11, 2020

(30) Foreign Application Priority Data
Jun. 21, 2016   (EP) ..................................... 16175453

(51) Int. Cl.
*G01N 35/00* (2006.01)
(52) U.S. Cl.
CPC .................. *G01N 35/00584* (2013.01); *G01N 2035/0097* (2013.01); *G01N 2035/00346* (2013.01)

(58) Field of Classification Search
CPC ... G01N 35/00584; G01N 2035/00346; G01N 2035/0097; G01N 33/5302; G01N 33/52; G01N 33/54366; G01N 21/75
See application file for complete search history.

(56) References Cited

U.S. PATENT DOCUMENTS 6,303,325 B1   10/2001   Mehta
6,663,833 B1   12/2003   Stave
(Continued)

FOREIGN PATENT DOCUMENTS

CN   101443656 A   5/2009
CN   105378465 A   3/2016
(Continued)

OTHER PUBLICATIONS

Serra, P.A. et al "Chapter 14: Design and Construction of a Distributed Sensor NET for Biotelemetric Monitoring of Brain Energetic Metabolism using Microsensors and Biosensors", Biosensors, Feb. 2010, pp. 241-260.
(Continued)

*Primary Examiner* — Jill A Warden
*Assistant Examiner* — John McGuirk
(74) *Attorney, Agent, or Firm* — Dugan & Dugan, PC (57) ABSTRACT

A system (1) for detecting an analyte of interest in a sample is disclosed that comprises a measurement chamber (21) for metering the sample and including a defined concentration of an activator (27) causing the generation of a product when interacting with the analyte of interest, a heating element (31) thermally coupled to the measurement chamber, a controller (33) adapted to control the heating element such that the measurement chamber is maintained at a defined temperature ($T_d$), a sensor (35) adapted to detect said product, a timer (37) adapted to time an interaction time between the sample and the activator; and a processor (39)

(Continued)

responsive to the sensor and the timer. The processor is adapted to, upon addition of the sample to the measurement chamber, determine an amount of the analyte of interest in the sample from a sensor signal indicative of an amount of said product in the measurement chamber provided by the sensor prior to termination of said interaction; known interaction kinetics between the analyte of interest and the activator at the defined temperature and the defined concentration; and the interaction time at time of generation of the sensor signal. A method of detecting an analyte of interest in a sample using such a system is also disclosed.

20 Claims, 4 Drawing Sheets

(56) References Cited

U.S. PATENT DOCUMENTS

| | | | |
|---|---|---|---|
| 8,383,421 | B2 | 2/2013 | Yanagida |
| 9,133,504 | B2 | 9/2015 | Hassibi |
| 2006/0211130 | A1* | 9/2006 | Macioszek ........... C12Q 1/6813 436/174 |
| 2007/0143669 | A1 | 6/2007 | Royer |
| 2007/0254372 | A1 | 11/2007 | Bickel |
| 2008/0039339 | A1* | 2/2008 | Hassibi ................ C12Q 1/6818 703/11 |
| 2009/0273354 | A1 | 11/2009 | Dhirani et al. |
| 2010/0173313 | A1 | 7/2010 | Bain et al. |
| 2014/0295415 | A1 | 10/2014 | Rolland |
| 2015/0001097 | A1 | 1/2015 | Malecha |

FOREIGN PATENT DOCUMENTS

| | | |
|---|---|---|
| WO | 2005108604 A2 | 11/2005 |
| WO | 2007143669 A1 | 12/2007 |
| WO | WO2007143669 A2 | 12/2007 |
| WO | 2008044214 A1 | 4/2008 |
| WO | 2008133075 A1 | 6/2008 |
| WO | WO2008133075 A1 | 6/2008 |
| WO | 2010035204 A1 | 4/2010 |
| WO | 2014080751 A1 | 5/2014 |
| WO | 2014144660 A1 | 9/2014 |
| WO | 2016079219 A1 | 5/2016 |

OTHER PUBLICATIONS

Noh, Hyeran et al "Fluidic Timers for Time-Dependent, Point-of-Care Assays on Paper", Analytical Chemistry , vol. 82, No. 19, pp. 8081-8078, 2010, Abstract Only.

Lewis, Gregory G. et al. "Point-of-Care Assay Platform for Quantifying Active Enzymes to Femtomolar Levels using Measurements of Time as the Readout", Analytical Chemistry , vol. 85, No. 21, pp. 10432-10439, Abstract Only.

* cited by examiner

ANALYTE DETECTION SYSTEM AND METHOD

CROSS-REFERENCE TO PRIOR APPLICATIONS

This application is the U.S. National Phase application under 35 U.S.C. § 371 of International Application No. PCT/EP2017/064913, filed on Jun. 19, 2017, which claims the benefit of European Patent Application No. 16175453.6, filed on Jun. 21, 2016. These applications are hereby incorporated by reference herein.

FIELD OF THE INVENTION

The present invention relates to a system for detecting an analyte of interest in a sample.

The present invention further relates to a method of detecting an analyte of interest in a sample with such a system.

BACKGROUND OF THE INVENTION

Point of care diagnostics is a rapidly growing area of medicine. The provision of diagnostic tools at the point of care allows for a rapid determination of data that can be used for diagnostic purposes, e.g. data of intermediate diagnostic relevance, in many cases without the need of the presence of a medical professional. Such diagnostic tools for example may be provided in the form of (disposable) assays, in which a user may insert a sample into a measurement chamber for the detection of (a concentration of) an analyte of interest in the sample using some binding agent or reagent. An example of such a diagnostic tool is an enzyme-linked immunosorbent assay, which may be used to detect the presence of an antigen of interest in the sample tested with the assay. In such an assay, the analyte of interest is detected following its interaction with an activator, e.g. an enzyme, causing the generation of a product that may be detected. Alternatively, some analytes of interest may be directly detected, e.g. glucose. Such detection may be achieved in any suitable manner, typically using some sort of sensor, e.g. an optical sensor for determining optical characteristics of the sample that are a function of the amount of analyte of interest present in that sample, a biosensor having a functionalized surface to which the analyte of interest may bind, thereby causing a change in a measurable parameter of the sensor such as its impedance or capacitance, and so on.

An example of such a diagnostic tool is disclosed in U.S. Pat. No. 9,133,504 B2, which discloses methods and systems for measuring the binding of analytes in solution to probes bound to surfaces in real-time. The method involves contacting a fluid volume having a plurality of different analytes with a solid substrate having a plurality of different probes. The probes are capable of specifically binding to the analytes. The method also involves measuring signals at multiple time points while the fluid volume is in contact with the substrate. The signals measured at multiple time points can be correlated with the amount of binding of the analytes with the probes. In this manner, the correlation may be determined on the fly. However, this requires substantial processing power, which may be undesirable from a cost perspective. What is more, the need to perform multiple measurements before the amount of binding of a particular analyte can be determined means that the measurement result may not be quickly available, which is also disadvantageous.

SUMMARY OF THE INVENTION

The present invention provides a system for detecting an analyte of interest in a sample that does not require calibration and that may rapidly produce a measurement result.

The present invention provides a method for detecting an analyte of interest in a sample that does not require calibration and that may rapidly produce a measurement result.

According to an aspect, there is provided a system for detecting an analyte of interest in a sample comprising a measurement chamber for metering the sample and including a defined concentration of an activator causing the generation of a product when interacting with the analyte of interest; a heating element thermally coupled to the measurement chamber; a controller adapted to control the heating element such that the measurement chamber is maintained at a defined temperature; a sensor adapted to detect said product; a timer adapted to time an interaction time between the sample and the activator; and a processor responsive to the sensor and the timer and adapted to, upon addition of the sample to the measurement chamber, determine an amount of the analyte of interest in the sample from a sensor signal indicative of an amount of said product in the measurement chamber provided by the sensor prior to termination of said interaction; known interaction kinetics between the analyte of interest and the activator at the defined temperature and the defined concentration; and the interaction time at time of generation of the sensor signal. The invention is based on the insight that by accurately controlling the amount of activator and the temperature at which the interaction between the analyte of interest and the activator takes place, a concentration of the analyte of interest in the sample may be detected prematurely, i.e. before all of the analyte of interest has interacted with the activator, e.g. reacted with the activator, bonded to the activator, and so on, due to the fact that for a specific analyte of interest the interaction kinetics, e.g. reaction rate or binding rate, with the activator are typically well-known at a given temperature. Hence, by accurately controlling the amount of sample, activator and the temperature at which the sample and activator interact, the amount of analyte of interest may be accurately determined from the interaction kinetics by timing the duration of the interaction between the analyte of interest and the activator and from the sensor signal provided with the sensor. This is particularly beneficial for analyte of interest that are typically abundant in the sample in relatively low concentrations, as for such analytes a relatively long interaction time may be required to complete the interaction between all the analyte and the activator, such that in such a scenario a substantial shortening of the time required to obtain the diagnostically relevant data with the system may be achieved.

In an embodiment, the measurement chamber is comprised by a disposable cartridge, the system further comprising an analysis unit comprising the heating element, the controller, the sensor, the timer, the processor and a cavity adapted to receive the disposable cartridge. This has the advantage that a large number of samples can be readily measured with the system, e.g. without requiring intermittent cleaning, by the use of the disposable cartridges in which the metered sample may be provided.

The processor may contain at least one of the controller and the timer. This reduces the number of discrete components within the system, thereby reducing its cost.

The system may further comprise a detector for detecting the addition of the sample to the measurement chamber, the timer being responsive to the detector. This ensures that the duration of the interaction between the analyte of interest and the activator is accurately determined.

The sensor may be adapted to generate the sensor signal in response to a control signal from the timer such that the sensor obtains the sensor signal at the desired point in time.

The analyte of interest may be a small molecule, an electrolyte, a blood gas, a protein or a nucleic acid.

An activator may be defined, as well-known in the art, as a molecule that increases the activity of a biological process that in his turn increases activity of cellular processes. In particular, an activator can bind to specific cellular receptor(s) setting the biological processes in motion (activates the cellular processes). The activator may be according to the invention, and as a way of examples, at least one of fMLP (formyl-methionyl-leucyl-phenylalanine), CRP (cAMP receptor protein), an antigen, an endogenous or exogenous danger-associated molecular pattern and a microbiological pathogen-associated molecular pattern.

"Danger" as used herein means, as well-known in the art, foreign to the human body, e.g. fMLP is derived from bacteria and can be called a danger molecule since the human body is alarmed by its presence.

"Pattern" as used herein may be related, as well-known in the art, to the specific moieties in amino acids or in DNA, like N-formyl-met (fM) or methylated DNA patterns.

In an embodiment, the product is human neutrophil lipocalin and the activator is fMLP.

According to another aspect, there is provided a method of detecting an analyte of interest in a sample with the system according to any embodiment of the present invention, the method comprising providing a measurement chamber containing a defined concentration of an activator causing the generation of a product when interacting with the analyte of interest; metering said sample by filling the measurement chamber with the sample; maintaining the measurement chamber at a defined temperature during the interaction between the analyte of interest and the activator with the heating element and timing an interaction time between the sample and the activator with the timer; sensing an amount of the product with the sensor after a defined interaction time; and determining an amount of the analyte of interest in the sample with the processor from the sensed amount of the product; known interaction kinetics between the analyte of interest and the activator at the defined temperature and the defined concentration; and the defined interaction time.

Such a method facilitates the rapid termination of an amount of the analyte of interest in the sample due to the fact that it is not necessary for all the analyte of interest to interact with the activator as previously explained.

The defined temperature may be in the range of 25-40° C., preferably wherein the defined temperature is in the range of 30-39° C., more preferably wherein the defined temperature is in the range of 36-38° C.

The defined concentration may be in the range of 0.003-0.3 µM, preferably wherein the defined concentration is in the range of 0.01-0.1 µM, more preferably wherein the defined concentration is in the range of 0.025-0.05 µM.

The defined interaction time may be less than 15 minutes, preferably wherein the defined interaction time is less than 10 minutes, more preferably wherein the defined interaction time is less than 5 minutes.

The sample may be a bodily fluid such as whole blood, derived blood samples containing neutrophils, plasma, serum, pus, urine or sweat.

The analyte of interest may be a small molecule, an electrolyte, a blood gas, a protein or a nucleic acid.

The activator may be at least one of fMLP (formyl-methionyl-leucyl-phenylalanine), CRP (cAMP receptor protein), an antigen, an endogenous or exogenous danger-associated molecular pattern and a microbiological pathogen-associated molecular pattern.

In an embodiment, the product is human neutrophil lipocalin and the activator is fMLP.

Providing a measurement chamber containing a defined concentration of an activator causing the generation of a product when interacting with the analyte of interest may comprise providing a disposable cartridge including the measurement chamber; and inserting the disposable cartridge in an analysis unit. This for instance has the advantage that the measurement chamber does not require cleaning in between samples.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
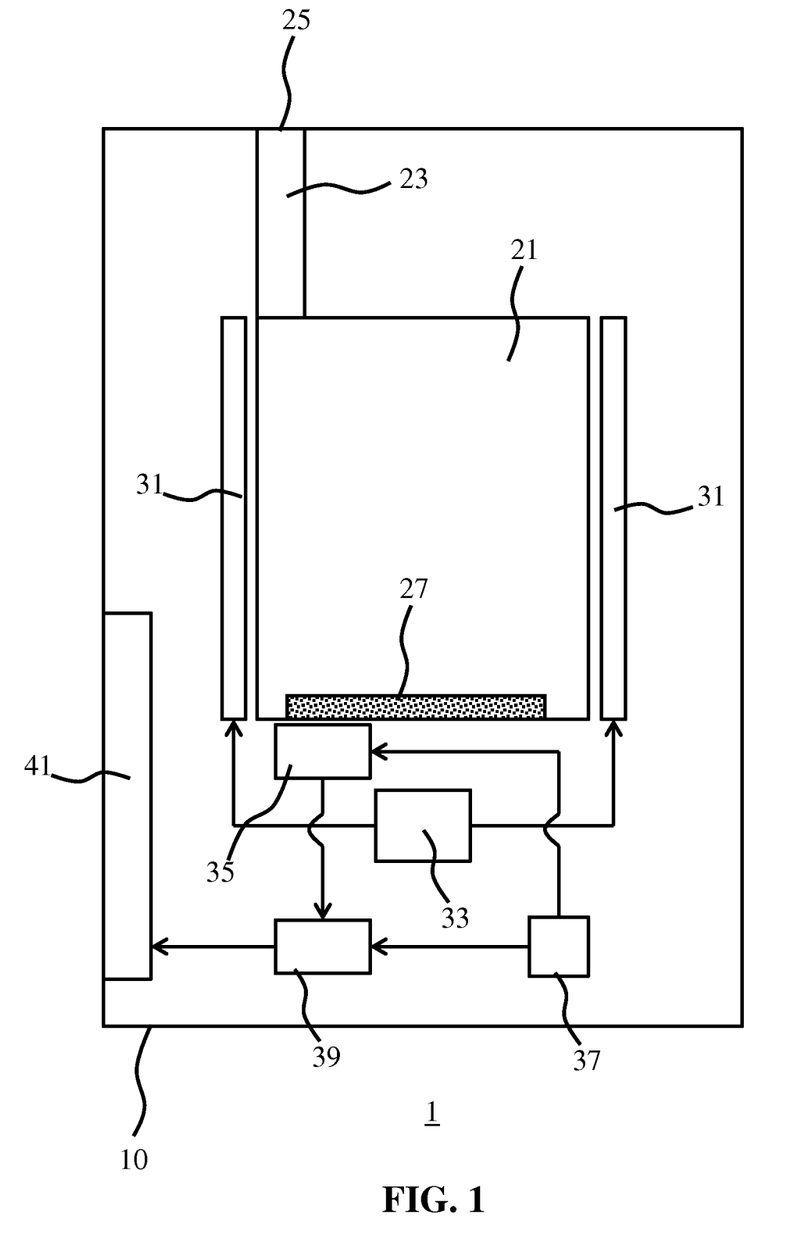
FIG. 1 schematically depicts a system for detecting an analyte of interest in a sample according to an embodiment.

FIG. 1 schematically depicts a system 1 for detecting an analyte of interest in a sample according to an embodiment. The system 1 comprises an analysis unit 10 and a measurement chamber 21, which may be an integral part of the analysis unit 10 or may be provided as a separate entity to be inserted into the analysis unit 10 as will be explained in more detail below. The measurement chamber 21 typically has a well-defined volume such that upon filling of the measurement chamber 21 with a sample potentially including an analyte of interest, the measurement chamber 21 comprises a metered volume of the sample, i.e. a volume corresponding to the volume of the measurement chamber 21. The sample may be inserted into the measurement chamber 21 through an opening 25 in fluid communication with the measurement chamber 21 through a fluid conduit 23. The opening 25 for example may be dimensioned to receive the nozzle of the syringe or the like such that the sample may be inserted into the measurement chamber 21 in a straightforward manner. Any suitable sample may be inserted into the measurement chamber 21. In some embodiments, this sample may be a bodily fluid sample such as for example a blood, plasma, serum, pus, urine or sweat sample.

The measurement chamber 21 further comprises an activator 27 for interacting with the analyte of interest in the sample such that a product is formed by the interaction of the activator 27 with the analyte of interest. For example, in case of a bodily fluid sample potentially comprising neutrophils indicative of the bodily fluid sample being extracted from a body site affected by inflammation or the like, such neutrophils may be stimulated by an activator such as fMLP to excrete a neutrophil lipocalin, e.g. human neutrophil lipocalin (HNL). Other types of activators for different types of analytes of interest are well-known per se. For example, the analyte of interest may be a small molecule, an electrolyte, a blood gas, a protein or a nucleic acid and so on, wherein the activator 27 may be at least one of fMLP (formyl-methionyl-leucyl-phenylalanine), CRP (cAMP receptor protein), an antigen, an endogenous or exogenous danger-associated molecular pattern and a microbiological pathogen-associated molecular pattern. Other examples will be immediately apparent to the skilled person. The activator 27 is typically presence in a defined amount within the measurement chamber 21 such that upon metering a sample in the measurement chamber 21, the activator 27 is present in a defined concentration. The activator 27 may be immobilized on an inner surface of the measurement chamber 21, e.g. on the floor of the measurement chamber 21, or may be placed in the measurement chamber 21 as a loose material, e.g. a powder or the like.

A heating element 31 is arranged in thermal contact with the measurement chamber 21 such that the heating element 31 can control the temperature in the measurement chamber 21, in particular when the metered sample is present in the measurement chamber 21. The heating element 31 may take any suitable shape and may be thermally coupled to the measurement chamber 21 in any suitable manner, e.g. by contacting one or more side surfaces and/or a bottom surface of the measurement chamber 21. The heating element 31 may be controlled by a controller 33. The controller 33 optionally may be responsive to a temperature sensor (not shown) in order to maintain the contents of the measurement chamber 21 at a desired (defined) temperature $T_d$. In case of the sample being a bodily fluid, the controller 33 may be adapted to maintain a constant temperature $T_d$ within the measurement chamber 21 within a temperature range of 25-40° C. The defined temperature $T_d$ may be the range of 30-39° C. in some preferred embodiments, and may be in the range of 36-38° C. in some more preferred embodiments. By controlling the temperature of the sample in the measurement chamber 21 such that the sample is kept at a temperature close to body temperature, characteristics of the sample, such as thermal stability of its components, its biological activity, and so on are well-maintained, thereby increasing the likelihood of a reliable measurement with the system 1.

The system 1 further comprises a sensor 35 adapted to detect the product of the interaction between the analyte of interest in the sample and the activator 27, such as for example HNL produced by neutrophils activated by fMLP. Such a sensor 35 for example may be an optical sensor, e.g. a sensor to detect fluorescence or the like of the product. To this end, the system 1 may further comprise a light source such as a laser, LED or the like to induce the fluorescence to be detected. The sensor 35 may form part of a detection arrangement as for instance disclosed in WO 2010/035204 A1, in which the sample or the activator 27 may contain magnetic beads that become fluorescent upon formation of the product, e.g. by binding of the analyte of interest in the sample to the activator 27, in which case the sensor 35 may be implemented as a photodetector for example. The details of this arrangement as described in WO 2010/035204 A1 may also be contemplated in embodiments of the present application. However, it should be understood that the sensor 35 is not limited to these embodiments and may be any suitable sensor as will be immediately apparent by the skilled person.

The system 1 further comprises a processor 39 responsive to the sensor 35, i.e. adapted to determine an amount of the analyte of interest from the sensor data provided by the sensor 35. The processor 39 may be implemented in any suitable manner, e.g. the processor 39 may be a general purpose processor programmed to provide the functionality that will be described in more detail below or may be a dedicated processor, e.g. an ASIC, a microprocessor or the like, specifically designed to implement this functionality. The processor 39 is further responsive to a timer 37 to provide the processor 39 with timing information regarding the dwell time of the sample in the measurement chamber 21, i.e. the duration of the interaction between the sample and the activator 27. At this point it is noted that the controller 33 and the timer 37 are shown as separate components by way of non-limiting examples only; it is for instance equally feasible that at least one of the controller 33 and the timer 37 forms an integral part of the processor 39. In an embodiment, the sensor 35 may be responsive to the timer 37; that is, the timer 37 may be adapted to deliver a sensor activation signal to the sensor 35 at a defined point in time, i.e. a predefined delay after the sample being inserted into the measurement chamber 21 such that the sensor 35 is triggered to take a measurement after the sample having been contact with the activator 27 for a defined period of time.

The sensor 35 in some embodiments may be further adapted to act as a detector for detecting the insertion of the sample into the measurement chamber 21, for example by detecting a change in optical transmittance in case of an optical sensor 35. Alternatively, a separate optical sensor (not shown) may be used as such a detector. Alternatively, a temperature sensor may be used as such a detector to detect a change in temperature in the measurement chamber 21 upon insertion of the sample into the measurement chamber 21. The timer 37 and/or the processor 39 may be responsive to this detector such that the start of the interaction period between the analyte of interest in the inserted sample and the activator 27 may be identified based on a detection signal provided by such a detector.

The system 1 may further comprise a display 41 or the like responsive to the processor 39 for displaying the determined amount of the analyte of interest in the sample as determined by the processor 39. Such a display 41 may be any suitable display, e.g. a LCD display, a LED display or the like, which may have a display screen under control of the processor 39 or may have one or more indicator elements for indicating a defined amount of the analyte of interest in the sample.

Figure 2:
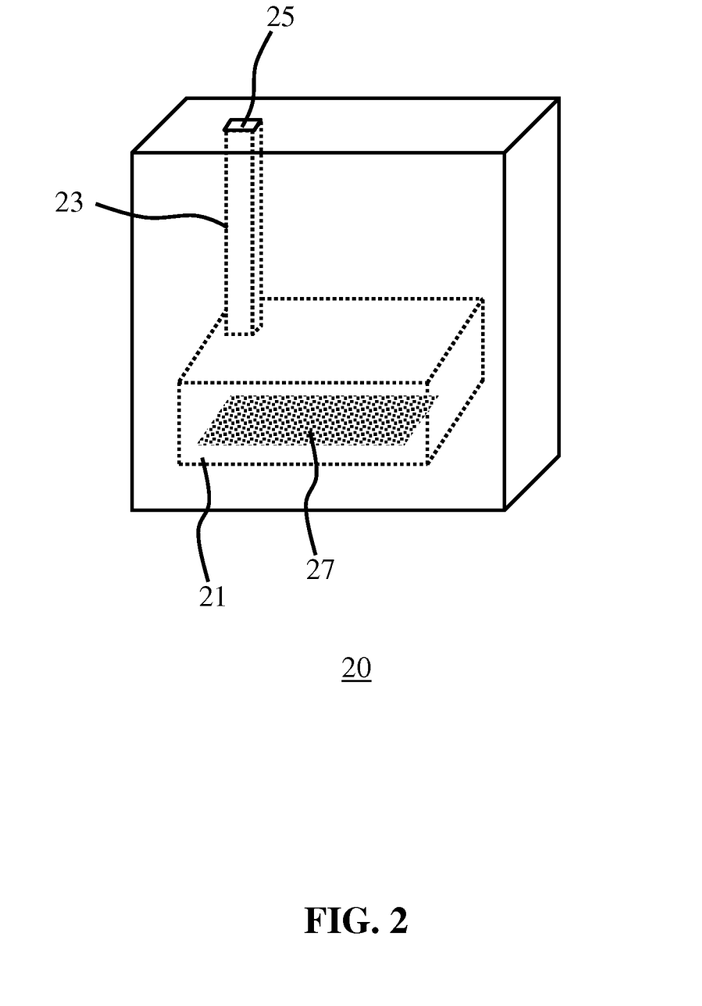
FIG. 2 schematically depicts an aspect of a system for detecting an analyte of interest in a sample according to another embodiment.
Figure 3:
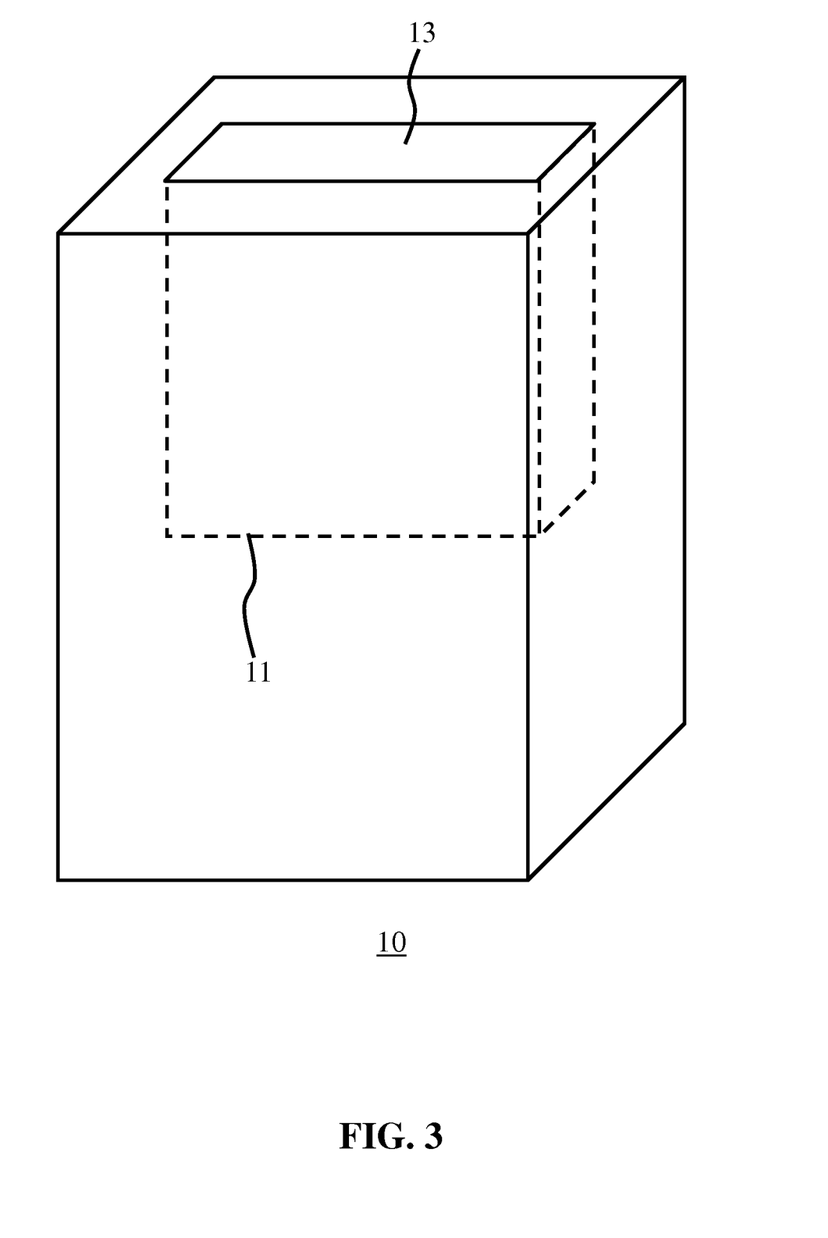
FIG. 3 schematically depicts another aspect of a system for detecting an analyte of interest in a sample according to another embodiment.

In a preferred embodiment, the measurement chamber 21 forms part of a disposable cartridge 20, e.g. a microfluidics cartridge of the like, which may be made of any suitable material, e.g. an optical grade polymer such as polycarbonate, PET, PMMA and the like. This is schematically depicted in FIG. 2. The remaining components of the system 1 may be contained in an analysis unit 10 as schematically depicted in FIG. 3 (the remaining components are not shown for the sake of clarity), with the analysis unit 10 comprising a recess 11 having an opening 13 for receiving the disposable cartridge 20. As will be readily understood by the skilled person, the recess 11 and opening 13 are typically dimensioned such that the disposable cartridge 20 fits into the recess 11 in a desired manner.

Figure 4:
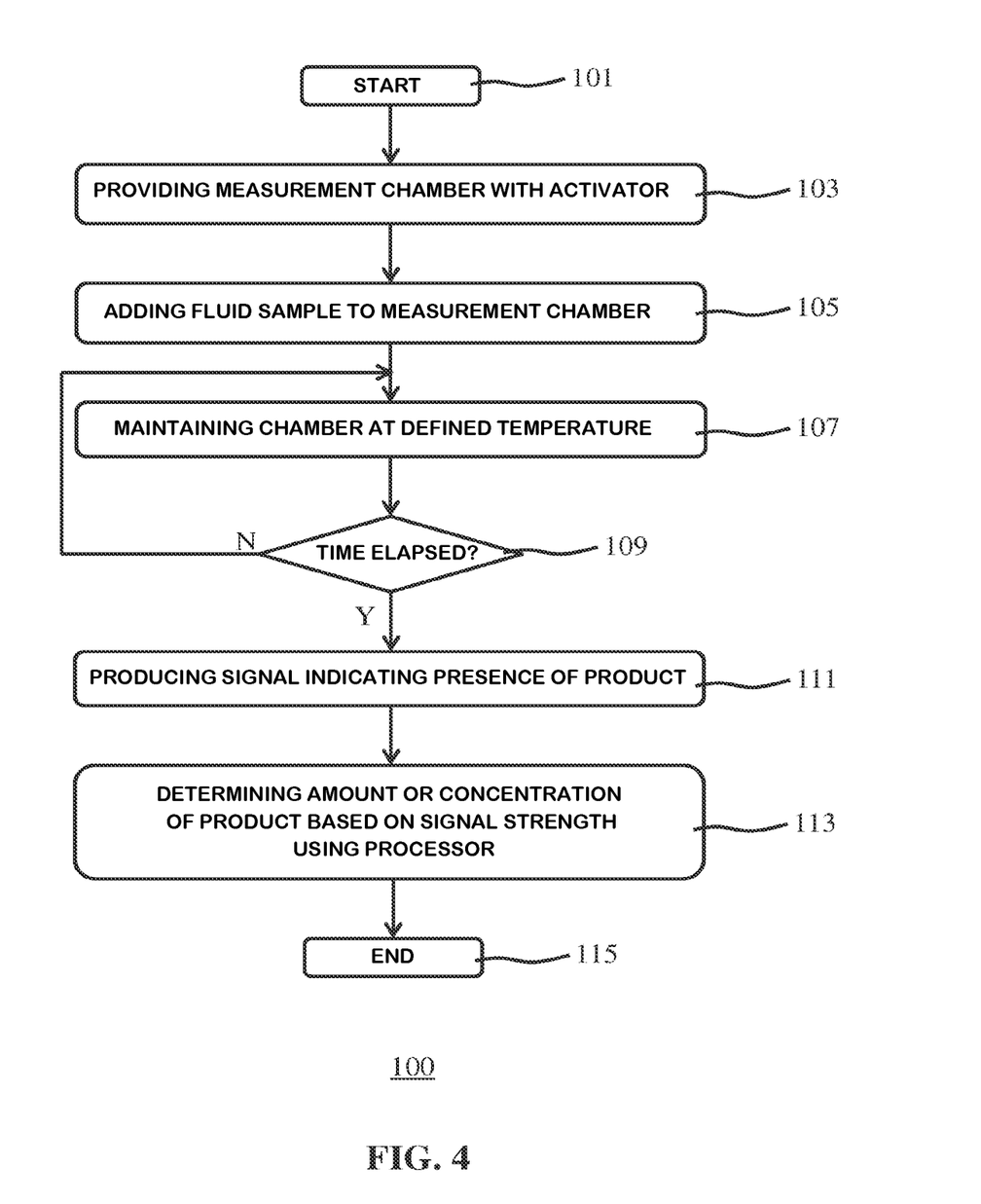
FIG. 4 is a flow chart of a method of detecting an analyte of interest in a sample with such a system according to an embodiment.

The system 1 may be adapted to implement an embodiment of the method 100 of detecting an analyte of interest in a sample, a flow chart of which is depicted in FIG. 4. The method 100 starts in 101, e.g. with switching on the system 1, after which the method 100 proceeds to 103 in which measurement chamber 21 including the activator 27 is provided. This may comprise adding a defined amount of activator 27 to the measurement chamber 21 although preferably the defined amount of activator 27 is already present in the measurement chamber 21, e.g. in free form or immobilized on an inner surface of the measurement chamber 21 as previously explained.

Next in 105 the sample, e.g. a bodily fluid sample, is added to the measurement chamber 21. Such a sample may contain an analyte of interest, e.g. neutrophils, with the activator 27 typically selected to interact with the targeted analyte of interest, causing the production of a product that is the result of this interaction. For example, in the case of the analyte of interest being neutrophils, the activator 27 may be fMLP triggering the neutrophils to excrete a neutrophil lipocalin, e.g. human neutrophil lipocalin (HNL). Step 15 may further comprise inserting a disposable cartridge containing the measurement chamber 21 including the metered sample into the analysis unit 10 of the system 1 as previously explained.

At the same time, the timer 37 may be started to monitor the dwell time of the sample in the measurement chamber 21, i.e. the time the analyte of interest in the sample has been exposed to the activator 27. Although it is noted that the analyte of interest may start to interact with the activator 27 before the measurement chamber 21 is completely filled, the timescales at which sufficient interaction between the analyte of interest and the activator 27 has taken place typically is several orders larger than the timescale for filling the measurement chamber 21 with the metered sample, such that the effects of the fill time of the measurement chamber 21 on the determination of the amount of analyte of interest in the sample may be ignored. This is particularly the case where the concentration of the analyte of interest in the sample is rather low. The timer 37 may be triggered to monitor the dwell time of the sample in the measurement chamber 21 by a detector of the system 1 that detects the insertion of the sample into the measurement chamber 21 as previously explained. The timer 37 may be directly triggered by the detector or may be triggered by the processor 39 in response to the processor 39 receiving a relevant detection signal from such a detector.

Upon insertion of the sample into the measurement chamber 21, the heating element 31 is engaged by the controller 33 in 107 to ensure that the sample in the measurement chamber 21 is kept at a constant temperature $T_d$, which typically is a temperature defined to ensure that the composition and biological activity of the sample is appropriately maintained as previously explained, e.g. a constant temperature in the vicinity of the body temperature of the body of a mammal, e.g. a human, from which the sample is taken. The controller 33 may be adapted to control the heating element 31 based on predetermined heat loss characteristics from the metered sample, such that the controller 33 is adapted to compensate for this heat loss. Alternatively, the controller 33 may be responsive to a temperature sensor that is thermally coupled to the measurement chamber 21, wherein the controller 33 is adapted to maintain the constant temperature $T_d$ in the measurement chamber 21 based on temperature sensor data provided by the temperature sensor.

Next, it is determined in 109 if sufficient time has elapsed after insertion of the sample into the measurement chamber 21 for the amount of analyte of interest in the sample to be determined. For example, the system 1 may be configured to determine the amount of analyte of interest in the metered sample after a fixed amount of time, in which case it may be checked in 109 if the timer 37 has reached a value indicative of this fixed amount of time. Alternatively, the sensor 35 may be periodically engaged to obtain a sensor reading of the product resulting from the interaction between the analyte of interest and the activator 27 in order to determine if the sensor signal strength of the sensor signal associated with this product has reached a minimum threshold, e.g. a threshold indicative of the signal being sufficiently stronger than a baseline signal strength, such that the concentration or amount of product in the metered sample may be accurately determined from the sensor data are provided by the sensor 35. As long as the amount of elapsed time is considered insufficient, the method 100 returns to 107 in which the metered sample is kept at a constant temperature $T_d$ as previously explained. Once it is determined in 109 the sufficient time has elapsed, the method 100 proceeds to 111 in which the sensor 35 senses the metered sample in the measurement chamber 21 at sample dwell time $t_m$ (which may be identical to the sufficient amount of time determined in 109) and produces a sensor signal, which sensor signal typically has a signal strength indicative of a detected amount of the product resulting from the interaction between the analyte of interest in the metered sample and the activator 27.

The method 100 subsequently proceeds to 113 in which the processor 39 determines the concentration or amount of the product P resulting from the interaction between the analyte of interest An and the activator Act. For the avoidance of doubt, such interaction may be a stimulus provided by the activator 27, e.g. acting as a catalyst, for the analyte of interest to produce the product P, a (reversible) binding reaction between the activator 27 and the analyte of interest in which the product P is the adduct of the activator 27 and the analyte of interest, a reaction product P from a reaction between the activator 27 and the analyte of interest, and so on.

The processor 39 is typically configured, e.g. programmed, to implement an algorithm in which the concentration or amount of the product P may be derived from the sensor data provided by the sensor 35 in 111. For example, the processor 39 may be configured to translate a sensor signal of a particular strength into a particular concentration or amount of the product P using a predetermined calibration or sensor response function. At this point, it is noted that the sensor signal captured at $t=t_m$ is typically captured whilst the interaction between the analyte of interest at the activator 27 has not yet completed or reached equilibrium. In other words, the determined amount or concentration of the product P by the processor 39 is not the final amount or concentration of the product P resulting from the completed (or equilibrium) interaction between the analyte of interest and the activator 27. However, as is well-known per se, the interaction kinetics, e.g. interaction rate, between species, here the analyte of interest and the activator 27, typically are a function of interaction temperature, interaction duration, analyte of interest concentration [A] and activator concentration [Act]. As will be understood from the foregoing, as the interaction temperature equals the defined temperature Td, the interaction duration equals the measurement time tm and the concentration [Act] of the activator 27 is predetermined by the amount of activator 27 and a metered volume of the sample in the measurement chamber 21, the only unknown variable is the concentration [A] of the analyte of interest in the metered sample. In other words, for an interaction between the analyte of interest and the activator 27 where the interaction takes place at a defined temperature for a defined amount of time using a defined concentration of the activator 27, the concentration [P] of the product P is directly correlated to the concentration [A] of the analyte of interest in the sample.

Consequently, the processor 39 is typically configured, e.g. programmed, with an algorithm expressing the known interaction kinetics between the analyte of interest and the activator 27 and to calculate the concentration [A] of the analyte of interest in the sample from the concentration [P] of the product in the sample as derived from the sensor signal provided by the sensor 35, the elapsed amount of time $t_m$ as provided by the timer 37, the defined temperature $T_d$, which may be a fixed temperature or may be provided to the processor 39 by the controller 33 and the predefined concentration [Act] of the activator 27 in the metered volume of the sample. In this manner, the processor 39 may be configured to rapidly determine the amount or concentration [A] of the analyte of interest (or indeed the amount or concentration [P] of the product) without requiring the interaction between the analyte of interest and the activator 27 to complete or reach equilibrium.

At this point, it is noted that such interaction kinetics are well-known per se and are not described in further detail for the sake of brevity only. As will be immediately apparent to the skilled person, depending on the type of interaction, a different interaction kinetic model may be required. As many different types of interaction kinetic models, e.g. based on different interaction or reaction orders, exist, it is simply not feasible to explain all these different types of models in some detail.

Upon determining the amount or concentration [A] of the analyte of interest in the metered sample, the processor 39 optionally may generate an indication of the determined amount or concentration [A]. This indication may be transmitted to a remote device, e.g. a remote receiver, using a transmission module (not shown) in the system 1, e.g. a wireless transmission module. Alternatively, the processor 39 may control the display 41 such that the indication is displayed on the display 41. Upon determining the amount or concentration [A] of the analyte of interest in the metered sample and the optional indication generation, the method 100 may terminate in 115.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A system for detecting an analyte of interest in a sample, comprising:
a measurement chamber for metering the sample and including a defined amount of an activator for causing the generation of a product when interacting with the analyte of interest, wherein upon metering of the sample into the measurement chamber, the activator is present in a defined concentration;
a heating element thermally coupled to the measurement chamber;
a controller adapted to control the heating element such that the measurement chamber is maintained at a defined temperature ($T_d$);
a sensor adapted to detect said product;
a timer adapted to time an interaction time between the sample and the activator; and
a processor responsive to the sensor and the timer and adapted to, upon addition of the sample to the measurement chamber, determine an amount of the analyte of interest in the sample from:
a single sensor signal indicative of an amount of said product in the measurement chamber provided by the sensor prior to termination of said interaction, such that when the single sensor signal is captured, the interaction between the analyte of interest and the activator has not yet completed or reached equilibrium;
known interaction kinetics between the analyte of interest and the activator at the defined temperature and the defined concentration; and
the interaction time at time of generation of the single sensor signal.

2. The system of claim 1, wherein the measurement chamber is comprised by a disposable cartridge, the system further comprising an analysis unit comprising the heating element, the controller, the sensor, the timer, the processor and a cavity adapted to receive the disposable cartridge.

3. The system of claim 1, wherein the processor contains at least one of the controller and the timer.

4. The system of claim 1, further comprising a detector for detecting the addition of the sample to the measurement chamber, the timer being responsive to the detector.

5. The system of claim 4, wherein the sensor is adapted to generate the single sensor signal in response to a control signal from the timer.

6. The system of claim 5, wherein:
the analyte of interest is an electrolyte, a blood gas, a protein or a nucleic acid; or
the activator is at least one of fMLP (formyl-methionyl-leucyl-phenylalanine), CRP (cAMP receptor protein), an antigen, an endogenous or exogenous danger-associated molecular pattern and a microbiological pathogen-associated molecular pattern.

7. The system of claim 6, wherein the product is human neutrophil lipocalin and the activator is fMLP.

8. A method of detecting the analyte of interest in the sample with the system of claim 1, the method comprising:
providing the measurement chamber containing the defined amount of the activator for causing the generation of the product when interacting with the analyte of interest;
metering said sample by filling the measurement chamber with the sample, wherein upon metering of the sample into the measurement chamber, the activator is present in a defined concentration;
maintaining the measurement chamber at the defined temperature during the interaction between the analyte of interest and the activator with the heating element and timing the interaction time ($t_m$) between the sample and the activator with the timer;
sensing the amount of the product with the sensor after a defined interaction time ($t_m$) prior to termination of said interaction, thereby capturing the single sensor signal, such that when the single sensor signal is captured, the interaction between the analyte of interest and the activator has not yet completed or reached equilibrium; and determining the amount of the analyte of interest in the sample with the processor from:

the sensed amount of the product;

known interaction kinetics between the analyte of interest and the activator at the defined temperature and the defined concentration; and the defined interaction time.

9. The method of claim 8, wherein the defined temperature is in the range of 25-40° C.

10. The method of claim 8, wherein the defined concentration is in the range of 0.003-0.3 µM.

11. The method of claim 8, wherein the defined interaction time is less than 15 minutes.

12. The method of claim 8, wherein the sample is a bodily fluid.

13. The method of claim 12, wherein:

the analyte of interest is an electrolyte, a blood gas, a protein or a nucleic acid; or the activator is at least one of fMLP (formyl-methionyl-leucyl-phenylalanine), CRP (cAMP receptor protein), an antigen, an endogenous or exogenous danger-associated molecular pattern and a microbiological pathogen-associated molecular pattern.

14. The method of claim 13, wherein the product is human neutrophil lipocalin and the activator is fMLP.

15. The method of claim 14, wherein providing the measurement chamber containing the defined amount of the activator for causing the generation of the product when interacting with the analyte of interest comprises:

providing a disposable cartridge including the measurement chamber; and inserting the disposable cartridge in an analysis unit.

16. The method of claim 8, wherein the defined temperature is in the range of 30-39° C.

17. The method of claim 8, wherein the defined temperature is in the range of 36-38° C.

18. The method of claim 8, wherein the defined concentration is in the range of 0.01-0.1 µM.

19. The method of claim 8, wherein the defined concentration is in the range of 0.025-0.05 µM.

20. The method of claim 8, wherein the defined interaction time is less than 5 minutes.

* * * * *